United States Patent
Millikin

(10) Patent No.: US 11,666,741 B1
(45) Date of Patent: Jun. 6, 2023

(54) METHOD FOR DELIVERING MATTER INTO THE HUMAN BODY

(71) Applicant: Rory Chesley Patrick Millikin, Kelowna (CA)

(72) Inventor: Rory Chesley Patrick Millikin, Kelowna (CA)

(73) Assignee: TruCelium Inc.

( * ) Notice: Subject to any disclaimer, the term of this patent is extended or adjusted under 35 U.S.C. 154(b) by 0 days.

(21) Appl. No.: 17/878,746

(22) Filed: Aug. 1, 2022

Related U.S. Application Data

(60) Provisional application No. 63/195,706, filed on Jun. 1, 2021.

(51) Int. Cl.
 *A61M 37/00* (2006.01)
 *A61M 5/142* (2006.01)

(52) U.S. Cl.
 CPC .............. *A61M 37/0015* (2013.01); *A61M 2005/14252* (2013.01); *A61M 2037/0061* (2013.01)

(58) Field of Classification Search
 CPC .... A61M 37/0015; A61M 2005/14252; A61M 2037/0061; A61M 2037/0023; A61M 2037/00; A61M 5/30
 See application file for complete search history.

(56) References Cited

U.S. PATENT DOCUMENTS

| | | | |
|---|---|---|---|
| 2002/0115957 A1* | 8/2002 | Sun ................ | A61M 37/0015 604/20 |
| 2004/0106894 A1* | 6/2004 | Hunter ............ | A61B 5/442 604/66 |
| 2007/0049901 A1* | 3/2007 | Wu ................ | A61M 37/0015 604/506 |
| 2007/0055214 A1* | 3/2007 | Gilbert ............ | A61M 5/30 604/500 |
| 2011/0105872 A1* | 5/2011 | Chickering, III .. | A61B 5/14514 600/573 |
| 2015/0246183 A1* | 9/2015 | Kavokin ......... | A61M 5/3286 604/176 |
| 2015/0305930 A1* | 10/2015 | Myung ............ | A61M 1/802 604/521 |
| 2016/0022905 A1* | 1/2016 | Nagar ............. | G16H 20/17 604/20 |
| 2016/0175408 A1* | 6/2016 | Chang ............ | A61K 38/4893 604/173 |
| 2017/0080164 A1* | 3/2017 | Kwon ............. | A61M 5/30 |
| 2019/0255253 A1* | 8/2019 | Yoh ............... | A61M 5/2053 |

* cited by examiner

*Primary Examiner* — Amber R Stiles
(74) *Attorney, Agent, or Firm* — Christopher Pilling

(57) ABSTRACT

A method for delivering matter into a human body is provided via a manual or automatic hand-held delivery device configured to provide a pressurized stream of fluid. The fluid contains compounds, chemicals, nutrients, vitamins or other desired matter. A user, via the device, is configured to target the pressurized stream of fluid to a location on the human body, e.g. the user's skin or mucosa. The pressurized stream is configured to penetrate the user's skin or mucosa such that at least a portion of the fluid is absorbed into the user's skin or mucosa. Various preconditioning methods are provided to increase the absorption rate and bioavailability.

11 Claims, 2 Drawing Sheets

METHOD FOR DELIVERING MATTER INTO THE HUMAN BODY

CROSS-REFERENCE TO RELATED APPLICATIONS

The present invention claims priority to provisional application Ser. No. 63/195,706 filed Jun. 1, 2021, which is hereby incorporated in its entirety at least by reference.

BACKGROUND OF THE INVENTION

1. Field of the Invention

The present invention relates to bioavailability and more particularly to a method for delivering matter into the human body.

2. Description of Related Art

Enhancing the bioavailability of compounds, chemicals, or matter (hereto referred to as the "Payload") into the human body is a desired goal of many industries, including pharmaceutical, chemical, nutritional, *cannabis*, or psychedelic based industries. Regarding psychedelics and *cannabis*, these substances have been used as a health supplement for over 1,000 years. It is well known that cannabinoids and psilocybin offer many benefits to users and the following disclosure provides a unique process in effectively providing a method to deliver these substances and other payloads into the human body.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

It is an object of the present invention to provide a delivery system and method of matter into the human body that does not include the standard needle syringe method.

In order to do so, a method for delivering matter into a human body is provided, the method comprising steps: (a) providing a delivery device configured to provide a pressurized stream of fluid, wherein the fluid contains compounds, chemicals, or nutrients; (b) targeting the pressurized stream of fluid to a location on the human body, via the delivery device, wherein the location is a user's skin or mucosa; and, (c) penetrating the user's skin or mucosa via the pressurized stream of fluid such that at least a portion of the fluid is absorbed into the user's skin or mucosa.

In one embodiment, the pressurized stream of fluid is at least two pressurized streams of fluid. In one embodiment, the pressurized stream of fluid has a radius between 20 nanometers to 20,000 nanometers. In one embodiment, the compounds, chemicals, or nutrients are configured to be encapsulated in a liposome, micelle, or phospholipid to increase absorption. In one embodiment, a step of applying heat at a temperature to the location to increase absorption is provided, wherein the step is performed prior to step (b). In one embodiment, a step of applying vibration to the location to increase absorption is provided, wherein the step is performed prior to step (b). In one embodiment, a step of applying chemicals to the location to increase absorption is provided, wherein the step is performed prior to step (b). In one embodiment, the delivery device comprises microneedles and further comprising a step of applying the microneedles to the location to increase absorption, wherein the step is performed prior to step (b). In one embodiment, the delivery device comprises a vacuum disk configured to create a vacuum seal on the human body, further comprising a step of creating a vacuum seal at the location to increase absorption, wherein the step is performed prior to step (b). In another embodiment, the vacuum disk is configured to pull the user's skin or mucosa. In another embodiment, the delivery device has a pressure adjustment control member configured to adjust the pressure (PSI) of the pressurized stream of fluid. In another embodiment, the radius of the stream is varied via a radius control member. In yet another embodiment, the temperature of the heat is adjustable. In one embodiment, the pressurized stream of fluid is generated via manual method or automatic method. In one embodiment, the manual method is a plunger. In another embodiment, the automatic method is a compressor pump. In another embodiment, the fluid is stored in a cartridge, wherein the cartridge is single use or reusable. In yet another embodiment, the delivery device is configured to hold multiple cartridges. In one embodiment, a step (d) capturing at least a portion of the fluid that is not absorbed into the user's skin or mucosa is provided, and repeating steps (b) and (c) with the captured portion of the fluid. In one embodiment, a further step of positioned a transdermal patch at the location to increase absorption, wherein the step is performed prior to step (b). In another embodiment, a step of applying light at the location to increase absorption is provided, wherein the step is performed prior to step (b).

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims.

BRIEF DESCRIPTION OF THE SEVERAL VIEWS OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable any person skilled in the art to make and use the invention and sets forth the best modes contemplated by the inventor of carrying out their invention. Various modifications, however, will remain readily apparent to those skilled in the art, since the general principles of the present invention have been defined herein to specifically provide a method for delivering matter into the human body.

For the purpose of this disclosure, the word "a" is defined to mean "at least one." The word "*cannabis*" is defined to mean "any species of the *cannabis* genus of flowing plants including *Cannabis sativa, Cannabis indica, Cannabis ruderalis*, and hemp." The terminology includes the words above specifically mentioned, derivatives thereof, and words of similar import. The word "plant or fungi matter" is defined to mean all mushrooms, *cannabis*, mycelium, or any other plant or fungi including vegetables, herbs, seeds, nuts, and any other edible plants." The word "compound(s)" is defined to mean any active ingredient including Psychedelics or *cannabis* which may include any of the following cannabinoids, Psilocin, psilocybin, Lysergic Acid Diethylamide, Baeocystin, N,N-Dimethyltryptamine, Tryptamine, Norbaeocystin, Mescaline, Muscimol, Ibotenic Acid, Lysergic Acid, Bufotenin, Beta-Carboline, Ethocybin, Indole Alkaloid, 2C-B, O-Acetylpsilocin, Ergine, 25l-NBOMe, Dipropyltryptamine, Diethyltryptamine, 2C-E, 4-Acetoxy-DiPt, Aeruginosin, Salvinorin A, 4-HO-DET, Diisopropyltryptamine, Glaucine, 4-HO-MET and 4-HO-DiPT, MDMA, Ketamine, Ayahuasca, LSD, and any other compound or chemical known to be a psychedelic or cannabinoid either from natural matter or synthetically designed. The word "matter" is defined as any substance, compound, chemical, nutrient, vaccine, medicine, herbal remedy, drug, vitamin, plant, etc. that is for use with the device/method of the present invention.

Figure 1:
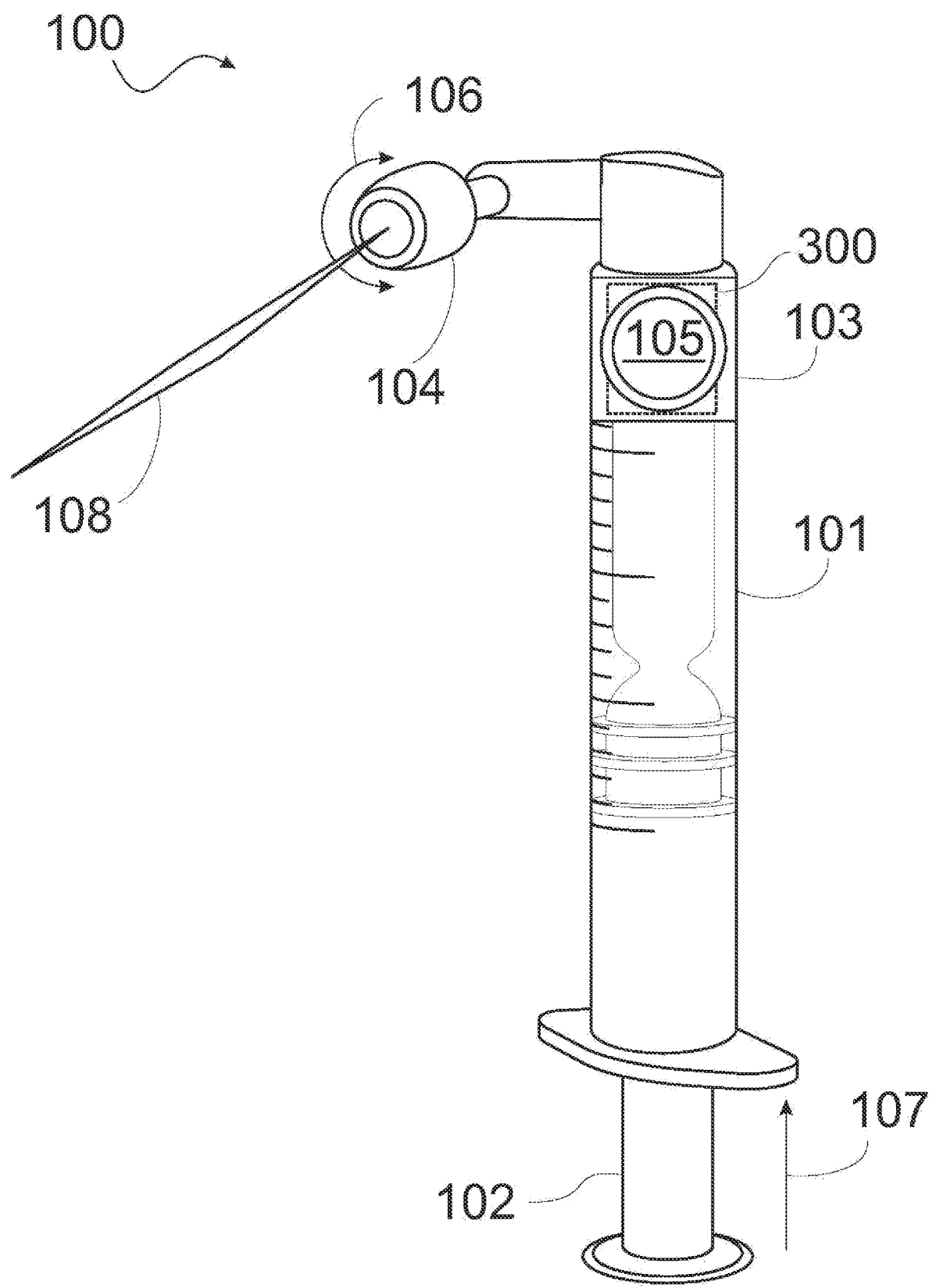
FIG. 1 is a delivery device configured to be used with the method of the present invention.

FIG. 1 is a delivery device configured to be used with the method of the present invention. Referring now to FIG. 1, the delivery device 100 is a manually powered hand-held device comprising a chamber 101, a plunger 102, and a nozzle 104. In some embodiments, the delivery device 100 includes a body portion 103 configured to house or accept a cartridge 300. The cartridge is configured to contain the matter intended to be delivered into the human body such as compounds, chemicals, or nutrients. The chamber 101 is attached and in fluid communication with the body portion 103.

During use, a user is configured to load one or more cartridges 300 into the body portion 103 of the device 100. Next, utilizing the plunger 102, the user can compress air (or liquid) into the chamber (adjusting the PSI) to a desired amount by pushing 107 the plunger into the chamber, then pressing the release button 105 to jettison the payload 108, i.e. release the fluid from the cartridge through the nozzle via the air pressure of the compressed air.

In some embodiments, there is a separate air chamber within the body portion with a one way valve enabling the user to continue activated the plunger repeatedly within the chamber to further increase the pressure. It should be understood this is just one example, and other mechanical methods may be provided to increase the air pressure within the body and/or chamber of the device.

In some embodiments, the nozzle 104 is adjustable, such that the nozzle opening is variable, wherein the nozzle opening size corresponding to the radius of the pressurized stream of fluid. In some embodiments, the user may rotate 106 the nozzle to adjust the opening size. In other embodiments, other methods may be used to adjust the nozzle opening size. In one embodiment, the radius may be adjusted between 20 nanometers to 20,000 nanometers.

The jettisoned payload or fluid delivery via device 100 is configured to be targeted to a user's exterior skin or mucosa, including but not limited to the user's back, arms, legs, oral cavities, buccal (check), vaginal, anal, gingiva, subdermal layers, etc. such that at least a portion of the payload penetrates the skin or mucosa enabling at least a portion of the matter/payload/fluid to be absorbed by the user. The pressure of the payload via the device 100 enhances the bioavailability. In preliminary testing, the bioavailability was increased up to 300% more using the pressurized stream of fluid of the present invention compared to applying the payload in a traditional manner, e.g. rubbing the matter on the skin. The cartridges 300 may be disposable or reusable. The pressurized stream of fluid may be liquid, gas, or a liquid gas combination.

The hand-held delivery device 100 of the present invention is easy to use, is a low cost, chemical free, and is dependable relying on mechanical principals and parts. However, an automatic hand-held delivery device 200 is provided in an alternative embodiment, wherein the automatic hand-held delivery device 200 has several features to further improve the bioavailability and absorption rate of the payload. This will be discussed in further details below.

Figure 2:
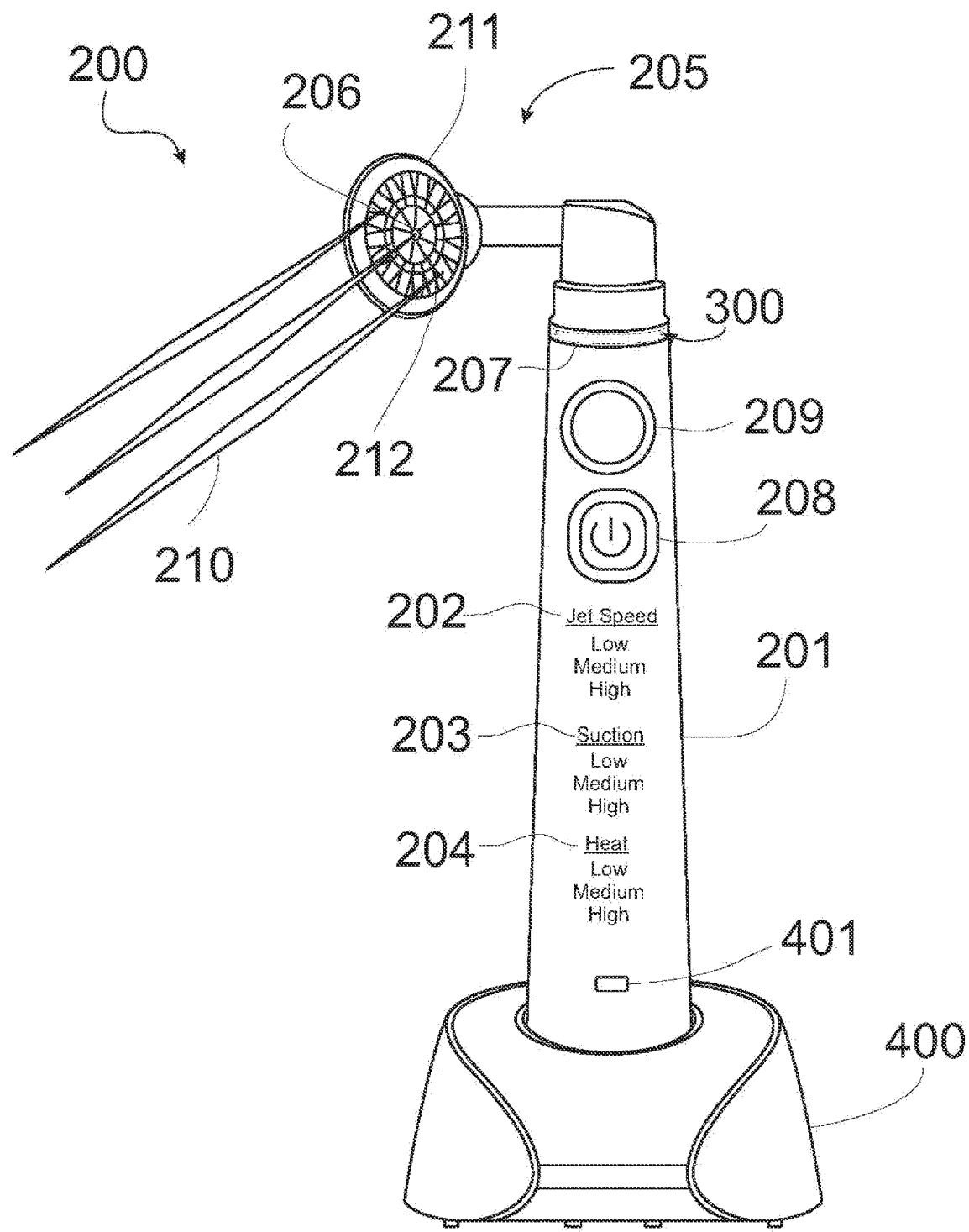
FIG. 2 is an alternative delivery device configured to be used with the method of the present invention.

Referring now to FIG. 2, the automatic hand-held delivery device 200 is illustrated. In one embodiment, the automatic hand-held delivery device 200 comprises an ergonomic handle or body member 201, wherein the body member 201 includes a number of different control members 202, 203, and 204, which will be discussed in greater details below. The automatic hand-held delivery device 200 further comprises a nozzle assembly 205, wherein the nozzle assembly includes nozzle 206 configured to deliver a pressurized stream of fluid. In some embodiments, the pressurized stream of fluid is at least two streams of fluid.

As with the previous described manually operated device, the automatic hand-held delivery device 200 includes the ability to load one or more cartridges 300 of matter within the body of the device. In some embodiments, the body member 201 and nozzle assembly 205 may be separated, via threading, magnetic connection, snap fit, etc. enabling the user to load the cartridge 300. In other embodiments, the cartridge 300 is inserted into a slot 207 between the body member 201 and nozzle assembly 205. As previously described, the cartridge 300 contains the matter or payload, such as vaccines, medications, vitamins, chemicals, compounds, nutrients, *cannabis*, psychedelics, etc.

In some embodiments, the automatic hand-held delivery device 200 comprises preconditioning features configured to improve absorption and the bioavailability of the payload. In one embodiment, a suction cup or disk 211 is provided on the nozzle assembly. The suction cup or disk is configured to create a seal or vacuum seal at the intended location, defined as the targeting location on the user, e.g. the user's skin or mucosa in which the payload is jettisoned for absorption into the body. Advantageously, the suction cup or disk, via seal or vacuum seal is configured to draw the capillaries of the user closer to the surface to increase the abortion rate or bioavailability via vasodilation or dilation. In some embodiments, the force or pressure of the suction is adjustable via a control member 203. In some embodiments, a heating feature is provided, wherein a portion of the nozzle assembly, such as the nozzle or suction cup may be heated via a temperature control member 204. In one embodiment, the heating feature adjusts the temperature of the pressurized stream of fluid, via an internal heating device. In yet another embodiment, the heating feature may be an external device, such as a heating pad. In one embodiment, microneedles 212 are provided on the nozzle assembly configured to be applied to the intended area (skin or mucosa) prior to the pressurized stream of fluid containing the payload. In some embodiments, additional preconditioning features are provided, including but not limited to lights or lasers configured to target the intended area (skin or mucosa) prior to the pressurized stream of fluid containing the payload. In additional embodiments, vibration may be used as a preconditioning method to increase the absorption and bioavailability rate. The vibration may be a setting that is controllable via the automatic hand-held delivery device 200, wherein the nozzle assembly or other portion of the device is configured to vibrate. The user may then apply the vibration to the targeted area prior to using the device. Further, in some embodiments, chemicals are applied to the targeted area to increase the absorption and bioavailability rate of the payload, wherein the chemicals may be applied via additional device/method, or be provided within the device, e.g. loaded and dispersible via the nozzle or other dispensing area prior to the payload. Yet in further embodiments, an additional step of positioning a transdermal patch on the user at the targeted area prior to using the device is provided. The transdermal patch configured to increase the absorption and bioavailability rate of the payload.

Advantageously, the automatic hand-held delivery device 200 has a built-in compressor or compressor pump, wherein the compressor or compressor pump is configured to compress the fluid, e.g. air or water, within the device such that the fluid can be combined with the payload positioned in the cartridge 300 and dispensed via the nozzle. In one embodiment, the payload release button 209 is configured to break the seal of the cartridge allowing the matter or payload to be combined within the pressured stream of fluid dispensed from the nozzle 206. The pressure of the compressed fluid is configured to be adjusted via control member 202. It should be understood that all the control members discussed herein may vary on the adjustment increments. In one embodiment, a "low", "medium", and "high" setting is provided, wherein the increments may include any desirable range found during experimentation and development as well known in the art.

In some embodiments, the automatic hand-held delivery device 200 includes an internal rechargeable battery configured to be charged in docking charger 400. Charging status lights 401 may be provided on the body of the delivery device 200. As previously discussed, in some embodiments, the user is enabled to adjust the radius of the pressured fluid stream, via nozzle rotation or other method. Further, as previously discussed, the number of fluid steams may vary.

In some embodiments, the payload is configured to be encapsulated in a liposome, micelle, or phospholipid to increase absorption. Any method known in the art may be used for encapsulation.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention. For example, although hand-held devices are discussed, it should be understood that a device that is not hand-held may be provided to carry out the claimed method without departing from the scope of the present invention.

In addition, reference to "first," "second," "third," and etc. members throughout the disclosure (and in particular, claims) are not used to show a serial or numerical limitation but instead are used to distinguish or identify the various members of the group.

What is claimed is:

1. A method for delivering matter into a human body, the method comprising steps:
    (a) providing a delivery device configured to provide a pressurized stream of fluid, wherein the fluid contains compounds, chemicals, or nutrients, wherein the delivery device comprises a nozzle assembly having microneedles and a vacuum element configured to create a vacuum seal on the human body;
    (b) creating, via the vacuum element, a vacuum seal at a location on the human body to increase absorption, wherein the location is a user's skin or mucosa;
    (c) applying the microneedles to the location to increase absorption;
    (d) targeting, via the nozzle assembly, the pressurized stream of fluid to the location; and,
    (e) penetrating, via the pressurized stream of fluid, the user's skin or mucosa such that at least a portion of the fluid is absorbed into the user's skin or mucosa; and,
    (f) capturing at least a portion of the fluid that is not absorbed into the user's skin or mucosa, and repeating steps (d) and (e) with the captured portion of the fluid.

2. The method of claim 1, further comprising a step of applying heat at a temperature to the location to increase absorption, wherein the step is performed prior to step (b).

3. The method of claim 1, further comprising a step of applying vibration to the location to increase absorption, wherein the step is performed prior to step (b).

4. The method of claim 1, further comprising a step of applying chemicals to the location to increase absorption, wherein the step is performed prior to step (b).

5. The method of claim 1, wherein the vacuum element is a disk configured to pull the user's skin or mucosa.

6. The method of claim 1, wherein the pressurized stream of fluid is generated via a manual method or an automatic method.

7. The method of claim 6, wherein the manual method is a plunger.

8. The method of claim 6, wherein the automatic method is a compressor pump.

9. The method of claim 1, further comprising a step of positioned a transdermal patch at the location to increase absorption, wherein the step is performed prior to step (d).

10. The method of claim 1, further comprising a step of applying light at the location to increase absorption, wherein the step is performed prior to step (d).

11. A method for delivering matter into a human body, the method comprising steps:
    (a) providing a delivery device configured to provide a pressurized stream of fluid, wherein the fluid contains compounds, chemicals, or nutrients;
    (b) targeting the pressurized stream of fluid to a location on the human body, via the delivery device, wherein the location is a user's skin or mucosa; and, (c) penetrating the user's skin or mucosa via the pressurized stream of fluid such that at least a portion of the fluid is absorbed into the user's skin or mucosa; and,
(d) capturing at least a portion of the fluid that is not absorbed into the user's skin or mucosa, and repeating steps (b) and (c) with the captured portion of the fluid.

* * * * *